(12) United States Patent
Angst et al.

(10) Patent No.: US 9,980,479 B2
(45) Date of Patent: May 29, 2018

(54) METHOD OF REDUCING NEMATODE DAMAGE

(75) Inventors: Max Angst, Basel (CH); Elmar Kerber, Dielsdorf (CH); Adel Morcos, Giza (EG)

(73) Assignee: Syngenta Crop Protection, LLC, Greensboro, NC (US)

( * ) Notice: Subject to any disclaimer, the term of this patent is extended or adjusted under 35 U.S.C. 154(b) by 2569 days.

(21) Appl. No.: 11/569,165

(22) PCT Filed: Jun. 6, 2005

(86) PCT No.: PCT/EP2005/006057
§ 371 (c)(1),
(2), (4) Date: Jun. 30, 2008

(87) PCT Pub. No.: WO2005/120232
PCT Pub. Date: Dec. 22, 2005

(65) Prior Publication Data
US 2008/0254013 A1 Oct. 16, 2008

(30) Foreign Application Priority Data
Jun. 7, 2004 (EP) .................................... 04013338

(51) Int. Cl.
| A01N 25/00 | (2006.01) |
| A01N 37/44 | (2006.01) |
| A01N 43/90 | (2006.01) |
| A01N 43/16 | (2006.01) |
| A01N 43/54 | (2006.01) |

(52) U.S. Cl.
CPC ............. *A01N 25/00* (2013.01); *A01N 37/44* (2013.01); *A01N 43/16* (2013.01); *A01N 43/54* (2013.01); *A01N 43/90* (2013.01)

(58) Field of Classification Search
CPC .... A01N 2300/00; A01N 43/16; A01N 43/90; A01N 37/44; A01N 47/34; A01N 53/00; A01N 25/00; A01N 25/02; A01N 25/04; A01N 25/08; A01N 25/12; A01N 25/14; A01N 41/10; A01N 43/54
See application file for complete search history.

(56) References Cited

U.S. PATENT DOCUMENTS

| 569,348 A | 10/1896 | Phillips |
| 639,879 A | 1/1899 | Winans |
| 3,303,090 A | 2/1967 | Huffman et al. |
| 3,442,922 A | 5/1969 | Langer |
| 3,971,781 A | 7/1976 | Diveley |
| 4,116,663 A * | 9/1978 | Ballou ............................. 71/23 |
| 4,191,551 A | 3/1980 | Cupery |
| 4,624,695 A | 11/1986 | Swerdloff et al. |
| 4,766,113 A | 8/1988 | West et al. |
| 5,447,945 A | 9/1995 | Sutter et al. |
| 5,595,748 A * | 1/1997 | Hewlett et al. ............... 424/405 |
| 5,696,094 A | 12/1997 | Yamashita |
| 5,733,566 A | 3/1998 | Lewis |
| 5,797,976 A * | 8/1998 | Yamashita ....................... 71/26 |
| 5,912,207 A | 6/1999 | Scher et al. |
| 6,060,074 A | 5/2000 | Butler, Jr. et al. |
| 6,110,904 A | 8/2000 | Warrior et al. |
| 6,335,308 B1 | 1/2002 | Kitten |
| 6,406,690 B1 | 6/2002 | Peleg et al. |
| 6,492,301 B1 | 12/2002 | Hacker et al. |
| 6,509,354 B1 | 1/2003 | Toriyabe et al. |
| 6,569,809 B1 | 5/2003 | Sato et al. |
| 6,569,810 B1 * | 5/2003 | Fischer et al. ................. 504/290 |
| 6,653,288 B1 * | 11/2003 | Beuvry ................ A61K 9/0019 424/422 |
| 6,670,494 B1 * | 12/2003 | Trusovs .......................... 556/49 |
| 7,445,791 B2 * | 11/2008 | Jadhav .................... A01N 51/00 424/405 |
| 8,232,265 B2 * | 7/2012 | Rogers .................. A61K 9/143 514/183 |
| 8,278,245 B2 * | 10/2012 | Hopkinson ............ A01N 25/02 504/116.1 |
| 8,765,160 B2 * | 7/2014 | Guyon ................... A01N 25/12 424/400 |

(Continued)

FOREIGN PATENT DOCUMENTS

| BE | 838720 | 8/1976 |
| CH | 481676 | 11/1969 |

(Continued)

OTHER PUBLICATIONS

McSorley et al. "Population Fluctuations of Plant-Parasitic Nematodes on Bananas in Florida" Proc. Fla. State Hort. Soc., 1981, 94, pp. 321-323.*
Haertl, E.J., "Metal Chelates in Plant Nutrition", Agricultural and Food Chemistry, 1963, 11(2), pp. 108-111.*
Lee et al., Xenobiotica, 1997, 27, 5, 423-429.

(Continued)

*Primary Examiner* — Christopher R Tate
*Assistant Examiner* — Aaron J Kosar
(74) *Attorney, Agent, or Firm* — James Cueva

(57) ABSTRACT

A method of reducing damage to plant propagation material and plant organs which grow at a later time by a representative of the class Nematode, which method comprises (I) treating the propagation material with (A) a chelating agent, and optionally (B) a macrocyclic lactone compound or another pesticide, before the material is sown or planted, or (II) applying (A) a chelating agent, and optionally (B) a macrocyclic lactone compound or another pesticide, to the locus of the material or the treated material defined in (I) before its planting, and/or at its planting and/or during its growth.

6 Claims, No Drawings

(56) References Cited

U.S. PATENT DOCUMENTS

| | | | | |
|---|---|---|---|---|
| 8,802,596 | B2* | 8/2014 | Rogers | A61K 9/143 504/206 |
| 8,975,213 | B2* | 3/2015 | Levy | A01N 63/04 504/100 |
| 9,161,545 | B2* | 10/2015 | Levy | A01N 63/04 |
| 2002/0064547 | A1 | 5/2002 | Chern et al. | |
| 2002/0136780 | A1 | 9/2002 | Batarseh | |
| 2003/0026846 | A1 | 2/2003 | Hei et al. | |
| 2004/0062785 | A1* | 4/2004 | Parker | 424/410 |
| 2004/0102324 | A1 | 5/2004 | Annis et al. | |
| 2013/0231299 | A1* | 9/2013 | Angst et al. | 514/30 |

FOREIGN PATENT DOCUMENTS

| | | | |
|---|---|---|---|
| CN | 1315309 | A | 10/2001 |
| DE | 1939687 | | 3/1970 |
| DE | 19904703 | A1 | 8/2000 |
| EP | 0445867 | A1 | 9/1991 |
| EP | 0552084 | A1 | 1/1993 |
| EP | 1258191 | | 11/2002 |
| EP | 1402776 | A1 | 3/2004 |
| FR | 1578111 | | 8/1969 |
| FR | 2716075 | | 8/1995 |
| FR | 2803176 | A1 | 7/2001 |
| GB | 2207866 | A | 2/1989 |
| GB | 2283677 | | 5/1995 |
| GB | 2380132 | A | 4/2003 |
| GB | 2386067 | A | 9/2003 |
| JP | 63270607 | | 11/1988 |
| JP | 105755 | A | 1/1998 |
| JP | 1112116 | A | 1/1999 |
| JP | 3047105 | B2 | 3/2000 |
| JP | 2000/119115 | A | 4/2000 |
| JP | 2003/081987 | A | 3/2003 |
| NZ | 330685 | | 1/2000 |
| WO | 84/01490 | A1 | 4/1984 |
| WO | 89/10693 | A1 | 11/1989 |
| WO | 95/17817 | A1 | 7/1995 |
| WO | 95/29589 | A1 | 11/1995 |
| WO | 95/31903 | A1 | 11/1995 |
| WO | 95/35031 | A1 | 12/1995 |
| WO | 97/02747 | A1 | 1/1997 |
| WO | 97/22246 | A1 | 6/1997 |
| WO | 97/31527 | A1 | 9/1997 |
| WO | 97/32476 | A1 | 9/1997 |
| WO | 98/22543 | A1 | 5/1998 |
| WO | 98/58546 | A1 | 12/1998 |
| WO | 99/00345 | A1 | 1/1999 |
| WO | 99/09997 | A1 | 3/1999 |
| WO | 99/39575 | A2 | 8/1999 |
| WO | 99/64156 | A1 | 12/1999 |
| WO | 00/62618 | A1 | 10/2000 |
| WO | 01/44236 | A1 | 6/2001 |
| WO | 03/073856 | A1 | 9/2003 |
| WO | 2004/028272 | A2 | 4/2004 |
| WO | 2004043445 | | 5/2004 |

OTHER PUBLICATIONS

Chung et al., Food and Chemical Toxicology, 2002, 40, 5, 723-729.
OA for Indian patent application No. 3830/CHENP/2009 mailed on Apr. 12, 2017, 8 pages.

* cited by examiner

METHOD OF REDUCING NEMATODE DAMAGE

This application is a 371 of International Application No. PCT/EP2005/006057 filed Jun. 6, 2005, which claims priority to EP 04013338.1 filed Jun. 7, 2004, the contents of which are incorporated herein by reference.

The present invention relates to methods of improving the plant growth, methods of reducing soil-inhabiting pests, such as nematodes, attack on plant propagation material and plant organs which grow at a later time, and agrochemical combinations therefor.

The industry is continually seeking methods of improving the growth of plant. Chemicals are typically used (i) to control undesirable species (for example, pests, such as insects, or vegetation, e.g., weeds, or fungi) and (ii) to promote plant growth (e.g., by providing nutrients), and thereby improve the growth of plants.

Soil-inhabiting pests such as nematodes damage crops by direct feeding damage, by transmitting viruses and by facilitating bacterial and fungal infections. The damage caused by nematodes to crops is often unspecific and easily confused with drought, malnutrition or disease. Typical symptoms are wilting, yellowing of the foliage and uneven or stunted growth.

Methods to control nematodes and thereby protect the plant include (1) use of nematicides (such as aldicarb), including the use of seed treatment nematicide (e.g. abamectin), and fumigants (e.g., methyl bromide), (2) use of soil steaming, (3) use of crop rotation practices, which is effective against nematodes that are specific to a particular crop; however, nematodes that have different hosts cannot be controlled by this method, and (4) use of nematode resistant or tolerant crops, which have been developed by conventional breeding or recombinant DNA technology (genetically modified plants).

It has now been found that a compound capable of forming a chelate unexpectedly provides a reduction in the damage caused by nematodes to plant propagation material and plant organs which grow at a later time. Further, it can been seen that an improvement in the control of soil-inhabiting pests by pesticides is achieved with the use of a chelating agent.

Accordingly, in a first aspect, the present invention provides a method of reducing damage to plant propagation material and plant organs which grow at a later time by a representative of the class Nematoda, which method comprises (i) treating the propagation material with (A) a chelating agent, and optionally (B) a macrocyclic lactone compound or another pesticide, before the material is sown or planted, or (ii) applying (A) a chelating agent, and optionally (B) a macrocyclic lactone compound or another pesticide, to the locus of the material or the treated material defined in (i) before its planting, and/or at its planting and/or during its growth.

In the event (A) and (B) are used in (i) and (ii) defined in the first aspect, the treatment or application of (A) and (B) can be either simultaneously or in succession.

It has also been found that a soil treated with variable amounts of a pesticide, especially a macrocyclic lactone compound, and a chelating agent result in an unexpected improvement in plant growth and control of pests, particularly soil-inhabiting pests, such as nematodes. The benefit of the invention, therefore, can be attained (i) by treating the soil with a composition comprising the combination (macrocyclic lactone compound and a chelating agent) or (ii) by treating the soil either simultaneously or in succession with a macrocyclic lactone compound and chelating agent. Typically, the treatment of the soil with the combination, whether as a single composition or as individual components, can occur several occasions during the growth of a plant up to the harvest (i.e. before its planting, and/or at its planting and/or during its growth). Indeed, the treatment of a single composition and then the individual components in succession is also envisaged during the growth of a plant.

Therefore, in a second aspect, the present invention provides a method of improving the growth of a plant (for example to improve the yield of a crop harvest), which comprises (i) and (ii) as defined in the first aspect.

Further, it has been found that the chelating agent improves the control of soil-inhabiting pests by pesticides (e.g. insecticides, acaricides and nematicides), and accordingly the present invention also provides an agrochemical composition for applying to the locus of a crop plant or treatment of plant propagation material comprising (A) a chelating agent and (B) one or more pesticides (such as an insecticide, nematicide, acaricide), with the proviso that the composition consisting of, as active ingredients, abamectin and N-phosphonomethyl valine is excluded. Examples of suitable pesticides include the macrocyclic lactone compounds (B). Such a composition can be useful for the treatment (i) and application (ii) as defined in the first aspect.

In a further aspect, the present invention provides a method of protecting a plant propagation material and plant organs which grow at a later time by from attack by a representative of the class Nematoda, which method comprises (i) treating the propagation material with (A) a chelating agent, and (B) a nematicide, before the material is sown or planted, or (ii) applying (A) a chelating agent, and (B) a nematicide, to the locus of the material or the treated material defined in (i) before its planting, and/or at its planting and/or during its growth.

In an embodiment of the present invention, the chelating agent is applied by the method defined in (ii). Preferably the chelating agent is applied before the propagation material is planted and also during it growth up to harvest. The chelating agent is advantageously applied to the locus of the propagation material after its planting.

The invention is described in more detail below.

Soil-Inhabiting Pests

The invention is especially effective against soil-inhabiting pests, which can damage a crop in the early stages of plant development. For example, the compositions can be formulated to target representative of the class Insecta and representatives of the order Acarnia, examples of which include:

from the order Lepidoptera, for example, *Acleris* spp., *Aegeria* spp., *Agrotis* spp., *Alabama argillaceae*, *Amylois* spp., *Autographa* spp., *Busseola fusca*, *Cadra cautella*, *Chilo* spp., *Crocidolomia binotalis*, *Diatraea* spp., *Diparopsis castanea*, *Elasmopalpus* spp., *Heliothis* spp., *Mamestra brassicae*, *Phthorimaea operculella*, *Plutella xylostella*, *Scirpophaga* spp., *Sesamia* spp., *Spodoptera* spp. and *Tortrix* spp.;

from the order Coleoptera, for example, *Agriotes* spp., *Anthonomus* spp., *Atomaria linearis*, *Chaetocnema tibialis*, *Conotrachelus* spp., *Cosmopolites* spp., *Curculio* spp., *Dermestes* spp., *Diabrotica* spp., *Dilopoderus* spp., *Epilachna* spp., *Eremnus* spp., *Heteronychus* spp., *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae*, *Sitotroga* spp., *Somaticus* spp., *Tanymecus* spp., *Tenebrio* spp., *Tribolium* spp., *Trogoderma* spp. and *Zabrus* spp.;

from the order Orthoptera, for example, *Gryllotalpa* spp.;
from the order Isoptera, for example, *Reticulitermes* spp.;
from the order Psocoptera, for example, *Liposcelis* spp.;
from the order Anoplura, for example, *Haematopinus* spp., *Linognathus* spp., *Pediculus* spp., *Pemphigus* spp. and *Phylloxera* spp.;
from the order Homoptera, for example, *Eriosoma larigerum;*
from the order Hymenoptera, for example, *Acromyrmex, Atta* spp., *Cephus* spp., *Lasius* spp., *Monomorium pharaonis, Neodiprion* spp., *Solenopsis* spp. and *Vespa* spp.;
from the order Diptera, for example, *Tipula* spp.;
crucifer flea beetles (*Phyllotreta* spp.), root maggots (*Delia* spp.), cabbage seedpod weevil (*Ceutorhynchus* spp.) and aphids.

An especially important aspect of the invention is the control of pests of the class Nematoda using the compounds according to the invention. There are a variety of nematodes, Endoparasitic-, Semiendoparasitic- and Ectoparasitic nematodes; such as root knot nematodes, cyst-forming nematodes and also stem and leaf nematodes. The present invention is especially directed towards root knot nematodes.

Examples of nematode pests include the species *Meloidogyne* spp. (for example, *Meloidogyne incoginita* and *Meloidogyne javanica, Meloidogyne hapla, Meloidogyne arenari*), *Heterodera* spp. (for example, *Heterodera glycines*, (without the s) *Heterodera carotae, Heterodera schachtii, Heterodora avenae* and *Heterodora trifolii*), *Globodera* spp. (for example, *Globodera rostochiensis*), *Radopholus* spp. (for example, *Radopholus similes*), *Rotylenchulus* spp., *Pratylenchus* spp. (for example, *Pratylenchus neglectans* and *Pratylenchus penetrans*), *Aphelenchoides* spp., *Helicotylenchus* spp., *Hoplolaimus* spp., *Paratrichodorus* spp., *Longidorus* spp., *Nacobbus* spp., *Subanguina* spp. *Belonlaimus* spp., *Criconemella* spp., *Criconemoides* spp. *Ditylenchus* spp., *Ditylenchus dipsaci, Dolichodorus* spp., *Hemicriconemoides* spp., *Hemicycliophora* spp., *Hirschmaniella* spp., *Hypsoperine* spp., *Macroposthonia* spp., *Melinius* spp., *Punctodera* spp., *Quinisulcius* spp., *Scutellonema* spp., *Xiphinema* spp., and *Tylenchorhynchus* spp.

The nematode species *Meloidogyne* spp., *Heterodera* spp., *Rotylenchus* spp. and *Pratylenchus* spp. are especially well controlled by the chelating agents.

Chelating Agents

Chelating agents in the frame of the present invention are compounds containing at least two heteroatoms selected from O, N and S. Such chelating agents are capable of entrapping (or sequestering) either another compound or one or several metal atom cations. Preferred chelating agents are those capable of entrapping a metal cation.

The chelating agents which are used according to the present invention are thus either in the metallated form (a metal cation is entrapped or sequestered by the chelating agent), or in the unmetallated form (no metal cation or another compound is sequestered, or another non-metal compound is sequestered).

Examples of metal cations capable of being entrapped by the chelating agent are preferably selected from cations of the first transition metal series, especially Cr, Mn, Fe, Co, Ni, Cu and Zn, more especially Fe.

The chelating agents are also capable of forming acid addition salts, and those having at least one acidic group are capable of forming salts with bases. Suitable salts with bases are, for example, metal salts, such as alkali metal or alkaline earth metal salts, for example, sodium, potassium or magnesium salts. The chelating agents may furthermore entrap a metal cation and at the same time form a salt with one or several of the remaining acidic groups, as for example in $Fe^{3+}Na^{1+}(EDTA^{4-})$, wherein EDTA is ethylenediaminotetraacetic acid, or $Zn^{2+}Na_3^{1+}(DTPA^{5-})$, wherein DTPA is di-ethylenetriaminopentaacetic acid, or Na[FeEDDHA], wherein EDDHA is N,N'-ethylene-bis(hydroxyphenyl)glycine.

Chelating agents, therefore, generally comprise a plurality of groups selected from carboxylic acid, hydroxyl, thiol, amino, phosphoric acid, or derivatives thereof, such as salt derivative.

Examples of preferred chelating agents include amino polycarboxylic acid chelating agents, aromatic and aliphatic carboxylic acid chelating agents, amino acid chelating agents, ether polycarboxylic acid chelating agents, phosphoric acid chelating agents, hydroxycarboxylic acid chelating agents and dimethylglyoxime. The chelating agents may be in the form of the acid or salt.

Examples of aminopolycarboxylic chelating acids include N,N'-ethylenebis(hydroxyphenyl)glycines (EDDHA), ethylenediaminebis(2-hydroxy-methylphenylacetic acid) (EDDHMA), N,N'-ethylenebis(2-hydroxy-5-sulfophenyl)glycine (EDDHSA), ethylenediaminetetraacetic acid (EDTA), N-(2-hydroxyethyl)-ethylenediaminetetraacetic acid (HEDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), and glycoletherdiaminetetraacetic acid (GEDTA) ethylenediaminedisuccinic acid (EDDS) and salts thereof.

Examples of the aromatic or aliphatic carboxylic acid chelating agents to be used in the present invention include oxalic acid, succinic acid, pyruvic acid, salicylic acid and anthranilic acid, and salts, methyl esters and ethyl esters thereof.

Further, examples of the amino acid chelating agents to be used in the present invention include glycine, serine, alanine, lysine, cystine, cysteine, ethionine, tyrosine and methionine, and salts and derivatives thereof.

Furthermore, examples of the ether polycarboxylic acid chelating agents to be used in the present invention include compounds represented by the following formula, compounds similar to the compounds represented by the following formula and salts (e.g., sodium salt) thereof:

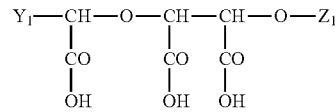

wherein $Y_1$ represents a hydrogen atom, a group represented by the formula —$CH_2COOH$ or a group represented by the formula —COOH, and $Z_1$ represents a hydrogen atom, a group represented by the formula —$CH_2COOH$ or a group represented by the formula

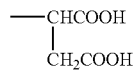

Examples of the hydroxy carboxylic acid chelating agents to be used in the present invention include malic acid, citric acid, glycolic acid, gluconic acid, heptonic acid, tartaric acid, lactic acid and salts thereof.

Examples of the electrolyte chelating agents of polymer (including oligomer) type to be used in the present invention include acrylic acid polymers, maleic anhydride polymers, α-hydroxyacrylic acid polymers, itaconic acid polymers, copolymers comprising at least two of the constituting monomers of these polymers and epoxysuccinic acid polymers.

In addition, chelating agents to be used in the present invention further include ascorbic acid and thioglycollic acid, and salts thereof.

The most preferred chelating agents are amino polycarboxylic acids, aliphatic carboxylic acids and hydroxycarboxylic acids.

Especially suitable chelating agents are compounds of the formula (II)

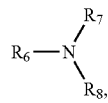
(II)

wherein $R_6$ is —$C_2$-$C_4$-alkyl-X—$C_1$-$C_6$-alkyl, —$C_2$-$C_4$-alkyl-X—$C_2$-$C_4$—X—$C_1$-$C_6$-alkyl, —$C_1$-$C_4$-alkyl-COOH, —$C_2$-$C_4$-alkyl-N($R_{10}$)$R_{11}$, —$C_2$-$C_4$-alkyl-X—$C_2$-$C_4$-alkyl-N($R_{10}$)$R_{11}$, —$C_2$-$C_4$-alkyl-X—$C_4$-$C_6$-alkyl-X—$C_2$-$C_4$-alkyl-N($R_{10}$)$R_{11}$, 2-hydroxyphenyl, 2-hydroxybenzyl, —CH[phenyl-substituted]COOH, pyrid-2-yl, pyrimidin-2-yl, —$CH_2$-pyrid-2-yl, —$CH_2$-pyrimidin-2-yl or

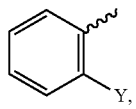

Y is OH or SH;

X is O, S or N($R_9$);

$R_7$, $R_8$, $R_9$, $R_{10}$ and $R_{11}$, are independently of each other hydrogen, $C_1$-$C_6$-alkyl, —$C_2$-$C_4$-alkyl-X—$C_1$-$C_6$-alkyl, —$C_2$-$C_4$-alkyl-X—$C_2$-$C_4$—X—$C_1$-$C_6$-alkyl, —$C_1$-$C_4$-alkyl-COOH, 2-hydroxyphenyl, 2-hydroxybenzyl, —CH[2-OH—$C_6H_4$]COOH, 2-pyridyl, 2-pyrimidinyl, —$CH_2$-pyrid-2-yl or —$CH_2$-pyrimidin-2-yl;

or $R_7$ and $R_8$ together are =CH—$R_{12}$;

or $R_{10}$ and $R_{11}$ together are =CH—$R_{12}$;

$R_{12}$ is phenyl which is ortho-substituted with O$R_{13}$ or S$R_{13}$;

phenyl-substituted is group of the formula

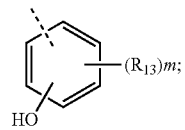

m is 1, 2 or 3; and $R_{13}$ is hydrogen or $C_1$-$C_6$-alkyl; and

Particularly preferred examples of chelating agents are N[—$C_1$-$C_4$-alkyl-COOH]$_3$ (NTA, nitrilotriacetic acid), [HOOC—$CH_2$—]$_2$NCH$_2$CH$_2$N[—CH$_2$—COOH]$_2$ (EDTA, ethylenediaminotetraacetic acid), HEDTA (N-(2-hydroxyethyl)-ethylenediaminetetraacetic acid), HOOC—$CH_2$—]$_2$NCH$_2$CH$_2$[HOOC—$CH_2$—]NCH$_2$CH$_2$N[—CH$_2$—COOH]$_2$ (DTPA, di-ethylenetriaminopentaacetic acid), and

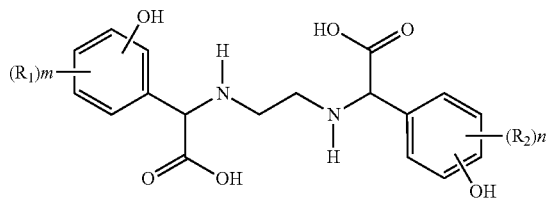

wherein $R_1$ and $R_2$ are selected from the group consisting of hydrogen, halogen, $C_1$-$C_6$alkyl, Halogen-$C_1$-$C_4$alkyl, $C_1$-$C_6$Alkoxy, Halogen-$C_1$-$C_6$alkoxy and —SO$_3$H, and m and n are independently of each other 1, 2 or 3, provided that each $R_1$ and $R_2$ can different if there should be more than one such substituent; especially preferred is a compound of the formula

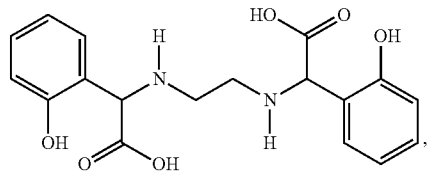
(o,o-EDDHA)

a compound of the formula

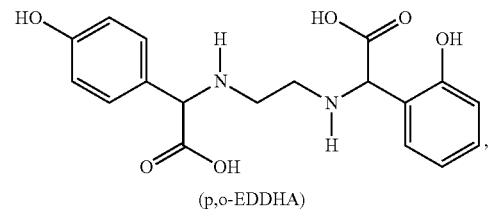
(p,o-EDDHA), a compound of the formula

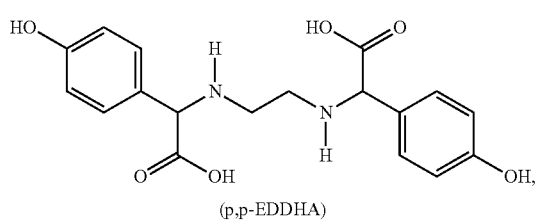
(p,p-EDDHA)

or any mixture thereof; and
a compound of the formula

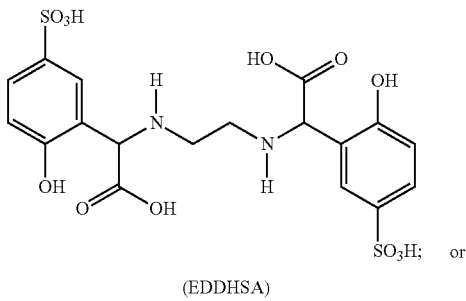 [SMILES: O=C(O)C(NCCNC(C(=O)O)c1cc(S(=O)(=O)O)ccc1O)c1cc(S(=O)(=O)O)ccc1O ; "(EDDHSA)"]
(EDDHSA)

a compound of the formula

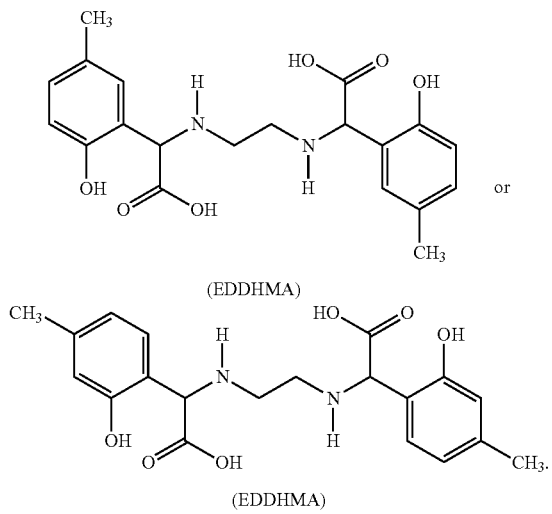
(EDDHMA)

(EDDHMA)

In an embodiment, the chelating agent is metallated with a transition metal cation, preferably iron (III) or iron (II), especially iron (III). Examples of commercial iron chelates include Sequestrene™, (a iron chelate Na[FeEDDHA]), Farben™, Greental™, Basafer™, Libfer™, Torneo™, Ferreostrene™, Pantafer™, Septamin™, Bolikel™, Hampiron™, Ferrilene™, Rexene™, and Folcidin™. Commercial samples of metallated chelating agents typically also contain a proportion of non-metallated chelating agent.

Especially preferred are iron chelates of a EDDHA, such as (o,o-EDDHA), (o,p-EDDHA), (p,p-EDDHA), or a mixture thereof. The iron content of a composition comprising an iron chelate is in general from 0.5 to 10, preferably from 1 to 8, in particular from 1.5 to 7, in particular from 2 to 6 or of from 2 to 5.5, especially from 2.4 to 5.5, percent by weight, based on the weight of the composition.

A preferred mixture of an iron chelate of EDDHA is that comprising (o,o-EDDHA) and (o,p-EDDHA). Preferably, the molar ratio of the (o,p-EDDHA) to (o,o-EDDHA) is greater than 0.8:1, particularly between 0.9:1 and 100:1. Especially, the ratio of o,p-EDDHA to o,o-EDDHA is from 1:1 to 50:1, or from 2:1 to 10:1, or from 0.9:1 to 2:1.

A composition comprising the chelating agent may comprise additional plant nutrients or plant fertilizers, these substances are preferably selected from the group including calcium sulfate $CaSO_4$, calcium nitrate $Ca(NO_3)_2 \cdot 4H_2O$, calcium carbonate $CaCO_3$, potassium nitrate $KNO_3$, magnesium sulfate $MgSO_4$, potassium hydrogen phosphate $KH_2PO_4$, manganese sulfate $MnSO_4$, copper sulfate $CuSO_4$, zinc sulfate $ZnSO_4$, nickel chloride $NiCl_2$, cobalt sulfate $CoSO_4$, potassium hydroxide KOH, sodium chloride NaCl, boric acid $H_3BO_3$ and metal salts thereof, $Na_2MoO_4$. The preferred additional nutrients may be present in an amount of 5% to 50% by weight, preferably of 10% to 25% by weight or of 15% to 20% by weight each. Preferred additional nutrients are urea, melamine, potassium oxide, and inorganic nitrates. The most preferred additional plant nutrient is potassium oxide. Where the preferred additional nutrient is urea, which may be present in an amount of 1% to 20% by weight, preferably of 2% to 10% by weight or of 3% to 7% by weight.

Use

Surprisingly, it has been found that the use of a chelating agent, especially in the metallated form, such as an agent chelating $Fe^{2+}$ or $Fe^{3+}$, to the locus of the crop plants results in a quite unexpected reduction in the nematode damage. The reduction in the damage provides enhanced plant growth characteristics, such as emergence, crop yield, protein content, more developed root system, tiltering increase, increase in plant height, bigger leaf blade, less dead basal leaves, stronger tillers, greener leaf color, less fertilizers needed, less seeds needed, less pesticides needed, more productive tillers, earlier flowering, early grain maturity, less plant verse (lodging), increased shoot growth, improved plant vigor, and early germination.

The chelating agent is applied to the locus of the plant one or more occasions during the growth of the plant. It can be applied to the planting site before the seed is sown, during the sowing of the seed, pre-emergence and/or post-emergence. The combination can also be used while the plant is being grown in a green house and the use can be continued after transplantation.

The use of the chelating agent can be via any suitable method, which ensures that the agent penetrates the soil, for example, nursery tray application, in furrow application, soil drenching, soil injection, drip irrigation, application through sprinklers or central pivot, incorporation into soil (broad cast or in band) are such methods.

The rate and frequency of use of the chelating agent on the plant may vary within wide limits and depends on the type of use, the specific chelating agent, the nature of the soil, the method of application (pre- or post-emergence, etc.), the plant or pest to be controlled, the prevailing climatic conditions, and other factors governed by the method of application, the time of application and the target plant.

Typical application rate of the chelating agent to the locus of the crop plant is from 45 to 10000 g per hectare (g/ha), especially from 90 to 5000 g/ha, preferably from 140 to 2000 g/ha, most preferably from 230 to 1000 g/ha. In the instance the chelating agent is a metallated chelate, such as iron EDDHA, application rate can be from 45 to 4800 g per hectare (g/ha), especially from 90 to 2400 g/ha, preferably from 140 to 1500 g/ha, most preferably from 230 to 950 g/ha. The agent may be applied once or several occasions during the growth of a plant depending on the plant and circumstances, for example, 1 to 6 or 1 to 4 occasions (for a tomato crop harvest, for example, the combination can be applied up to 4 times before harvest), and the amounts indicated above are for each application.

The plant propagation material can also be treated with the chelating agent before it is sown or planted, and then chelating agent can, optionally, be applied to the locus of the plant one or more occasions during the growth of the plant.

The term "plant propagation material" is understood to denote all the generative parts of the plant, such as seeds, which can be used for the multiplication of the latter and vegetative plant material such as cuttings and tubers (for example, potatoes). There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Further, the present invention is also applicable for use with a plant propagation material, e.g., plant seed, that has already undergone a treatment with a pesticide.

Even distribution of the chelating agent (and optionally one or more other pesticides) and adherence thereof to the seeds is desired during treatment of the propagation material, for example, a seed. The treatment could vary from a thin film of the formulation containing the chelating agent on a plant propagation material, such as a seed, where the original size and/or shape are recognizable to a thick film (such as a coating or pelleting with many layers of different materials (such as carriers, for example, clays; different formulations, such as of active ingredients; polymers; and colourants) where the original shape and/or size of the seed is no longer recognisable.

Accordingly, in an embodiment the chelating agent is adhered to the propagation material, such a seed.

In an embodiment, the chelating agent is present on the seed in a pellet form.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications).

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the pesticide is applied to the soil but would include any application practice that would target the seed during the sowing/planting process.

The treated plant propagation material of the present invention can be treated in the same manner as conventional plant propagation material.

The treated propagation material can be stored, handled, sowed and tilled in the same manner as any other pesticide treated material, such as seeds.

Preferably, the treatment occurs before sowing of the seed so that the seed being sown/planted has been pre-treated.

Typical application rates of a chelating agent to a propagation material also vary depending on the specific use. For a seed, the rates can be from 10 to 1000, preferably from 150 to 700, more preferably from 100 to 600, especially from 150 to 400, grams of chelating agent per hectare of seeds.

For a vegetable crop the chelating agent is typically applied in several occasions. For a fruit crop the chelating agent can also be applied in several occasions as in vegetables, however, a one shot application of a chelating agent (e.g., SEQUESTRENE) is generally sufficient.

Target crop plants for use in the present invention include especially field crops fruits, vegetables, nuts, berries, tropical plantations, ornamentals and others, such as wheat, barley, rye, oats, rice, maize, sorghum, beans, lentils, peas, soybeans, rape, mustard, poppy, sugar- and fodder-beet, cotton, flax, hemp, jute, sunflowers, castor oil, groundnuts, potatoes, tobacco, sugar cane, apples, pears, plums, peaches, nectarines, apricots, cherries, oranges, lemons, grapefruit, mandarins, olives vines, hops, almonds, walnuts, hazelnuts, avocado, bananas, tea, coffee, coconut, cocoa, natural rubber plants, oil plants, strawberries, raspberries, blackberries, spinach, lettuce, asparagus, cabbages, chinese kale, carrots, onions, tomatoes, cucumbers, pepper, eggplants, melons, paprika, chilli, roses, chrysanthemums and carnations.

The plants can also be genetically modified.

The present invention has been found to be especially effective in high pH (such as 7 to 8.5) soil types.

Normally, a grower in the management of his crop would use one or more other agronomic chemicals in combination with the chelating agent for the treatment (i) and application (ii) as defined in the first aspect. Examples of agronomic chemicals include pesticides, plant nutrients or plant fertilizers.

Suitable examples of plant nutrients or plant fertilizers are calcium sulfate $CaSO_4$, calcium nitrate $Ca(NO_3)_2 * 4H_2O$, calcium carbonate $CaCO_3$, potassium nitrate $KNO_3$, magnesium sulfate $MgSO_4$, potassium hydrogen phosphate $KH_2PO_4$, manganese sulfate $MnSO_4$, copper sulfate $CuSO_4$, zinc sulfate $ZnSO_4$, nickel chloride $NiCl_2$, cobalt sulfate $CoSO_4$, potassium hydroxide KOH, sodium chloride NaCl, boric acid $H_3BO_3$ and metal salts thereof, $Na_2MoO_4$. The nutrients may be present in an amount of 5% to 50% by weight, preferably of 10% to 25% by weight or of 15% to 20% by weight each. Preferred additional nutrients are urea, melamine, potassium oxide, and inorganic nitrates. The most preferred additional plant nutrient is potassium oxide. Where the preferred additional nutrient is urea, it is present in an amount of generally 1% to 20% by weight, preferably 2% to 10% by weight or of 3% to 7% by weight.

A single pesticide may have activity in more than area of pest control, for example, a pesticide may have fungicide, insecticide and nematicide activity. Specifically, aldicarb is known for insecticide, acaricide and nematicide activity, while metam is known for insecticide, herbicide, fungicide and nematicide activity.

Accordingly, the action of the chelating agent can be significantly improved and adapted to the given circumstances by the use of one or more pesticide compounds, such as a nematicide, insecticide and/or fungicide, used in agriculture, either as a seed treatment or application to the locus where the plant is grown.

Examples of pesticides include macrocyclic lactone compounds, which are compounds having a ring in its chemical structure made up of twelve or more atoms. The atoms may be selected from carbon, oxygen, nitrogen or sulfur, preferably the atoms are carbon and oxygen. In an embodiment, the ring has up to 20 atoms.

Examples of (B) include spinosad (737), avermectin and avermectin monosaccharide derivatives, such as abamectin (1), doramectin (25-cyclohexyl-5-O-demethyl-25-de(1-methylpropyl)avermectin $A_{1a}$; CAS RN 117704-25-3), emamectin (291), eprinomectin ((4"R)-4"-(acetylamino)-4"-deoxyavermectin $B_1$; CAS RN 123997-26-2), ivermectin (5-O-demethylavermectin Ala (i) mixture with 5-O-demethyl-25-de(1-methylpropyl)-25-(1-methylethyl)avermectin A$_{1a}$ (ii), CAS RN 70288-86-7 (70161-11-4+70209-81-3)) and selamectin ((5Z,25S)-25-cyclohexyl-4'-O-de(2,6-dideoxy-3-O-methyl-α-L-arabino-hexopyranosyl)-5-demethoxy-25-de(1-methylpropyl)-22,23-dihydro-5-(hydroxyimino)avermectin A$_{1a}$; CAS RN 165108-07-6), and milbemycin derivatives, such as milbemectin (557), milbemycin oxime ((6R,25R)-5-demethoxy-28-deoxy-6,28-epoxy-25-ethyl-5-(hydroxyimino)milbemycin B mixture with (6R,25R)-5-demethoxy-28-deoxy-6,28-epoxy-5-(hydroxyimino)-25-methylmilbemycin B), moxidectin ((6R,23E,25S)-5-O-demethyl-28-deoxy-25-[(1E)-1,3-dimethyl-1-butenyl]-6,28-epoxy-23-(methoxyimino)milbemycin B; CAS RN 113507-06-5), and SI0009 (a milbemycin B mixture of 5-O-demethyl-28-deoxy-6,28-epoxy-25-methyl-13-[[(methoxyimino)phenylacetyl]oxy]-(6R,13R,25R)-(9CI) and 5-O-demethyl-28-deoxy-6,28-epoxy-25-ethyl-13-[[(methoxyimino)phenylacetyl]oxy]-(6R,13R,25R)-(9CI); CAS RN 171249-10-8 and 171249-05-1).

The natural Avermectins, which can be obtained from *Streptomyces avermitilis*, are referred to as A1a, A1b, A2a, A2b, B1a, B1b, B2a and B2b. The compounds referred to as "A" and "B" have a methoxy radical and an OH group, respectively, in the 5-position. The "a" series and the "b" series are compounds in which the substituent R$_1$ (in position 25) is a sec-butyl radical and an isopropyl radical, respectively. The number 1 in the name of the compounds means that carbon atoms 22 and 23 are linked by double bonds; the number 2 means that they are linked by a single bond and that the C atom 23 carries an OH group.

In a preferred embodiment, the macrocyclic lactone lactone compound is an avermectin derivative, an avermectin monosaccharide derivative or a milbemycin derivative. Especially preferred are (i) avermectin B1 derivatives (such as B1a, B1b, and other substitutents on the 25-position); (ii) avermectin B derivatives having a single bond between carbon atoms 22 and 2; and the corresponding monosaccharide derivatives of (i) and (ii). Advantageously, abamectin is preferred as the macrocyclic lactone compound according to the present invention.

Derivatives of avermectin and avermectin monosaccharides can be obtained by chemical syntheses, and include those disclosed in WO02/068442, WO02/068441, WO03/020738, WO03/053988 and WO03/095468.

Examples of nematicides are abamectin, carbamate nematicides (e.g. aldicarb, carbofuran, carbosulfan, oxamyl, aldoxycarb, ethoprop benomyl, alanycarb), organophosphorus nematicides (e.g. phenamiphos, fenamiphos, fensulfothion, terbufos, fosthiazate, phosphocarb, dichlofenthion, isamidofos, fosthietan, isazofos, ethoprophos, cadusafos, chlorpyrifos, heterophos, isamidofos, mecarphon, phorate, thionazin, triazophos, diamidafos, phosphamidon), methyl bromide, methyl iodide, carbon disulfide, 1,3-dichloropropene, chloropicrin, cytokinins, dazomet, DCIP, ethylene dibromide, GY-81, metam, methyl isocyanate, *myrothecium verrucaria* composition, flupyrazofos, benchlothiaz, [2-cyanoimino-3-ethylimidazolidin-1-yl]phosphonothioic acid O-ethyl S-propyl ester, and *bacillus firmus*.

Abamectin, aldicarb, oxamyl, fenamiphos, ethoprophos, cadusafos, fosthiazate, 1,3-dichloropropene, chloropicrin and methyl bromide, methyl iodide are preferred nematicides for use in combination with the chelating agent.

Further, the chelating agent may also be used in combination with one or more pesticides to improve the pest control.

Suitable examples of pesticides that can be used include acephate (2), acetamiprid (4), acetoprole (1-[5-amino-1-[2,6-dichloro-4-(trifluoromethyl)phenyl]-4-(methylsulfinyl)-1H-pyrazol-3-yl]ethanone), aldicarb (16), alpha-cypermethrin (202), azinphos-methyl (45), azoxystrobin (47), benalaxyl (56), benalaxyl-M (methyl N-(2,6-dimethylphenyl)-N-(phenylacetyl)-D-alaninate), benclothiaz (7-chloro-1,2-benzisothiazole), bendicoarb (58), benfuracarb (60), benomyl (62), bensultap (66), bifenthrin (76), bitertanol (84), boscalid, (88) captan (114), carbendazim (116), carbaryl (115), carbofuran (118), carbosulfan (119), carboxin (120), carbpropamid (2,2-dichloro-N-[1-(4-chlorophenyl)ethyl]-1-ethyl-3-methylcyclopropanecarboxamide), chlorothalonil (142), chlorpyrifos (145), chlorpyrifos-methyl (146), clothianidin (165), copper salts (such as copper sulfate (172), cuprous oxide (181), Bordeaux mixture (87), copper hydroxide (169), copper sulfate (tribasic) (173), copper oxychloride (171) and copper octanoate (170)), cymoxanil (200), cypermethrin (201), cyproconazole (207), cyprodinil (208), cyromazine (209), dazomet (216), deltamethrin (223), diazinon (227), difenoconazole (247), dimethoate (262), dimoxystrobin (266), diniconazole (267), dinotefuran (271), Emamectin (291), endosulfan (294), ethaboxam (N-(cyano-2-thienylmethyl)-4-ethyl-2-(ethylamino)-5-thiazolecarboxamide), ethirimol (5-butyl-2-(ethylamino)-6-methyl-4(1H)-pyrimidinone), ethiprole (310), ethoprophos (312), famoxadone (322), fenamidone (325), fenamiphos (326), fenhexamid (334), fenpiclonil (341), fipronil (354), flonicamid (358), fluoxastrobin (382), fluazinam (363), fludioxonil (368), fluquinconazole (385), flutolanil (396), flutriafol (397), fonophos (O-ethyl S-phenyl ethylphosphonodithioate), fosetyl-aluminium (407), fuberidazole (409), furathiocarb (412), gamma-cyhalothrin (197), gamma-HCH (430), guazatine (422), heptenophos (432), hexaconazole (435), hymexazol (447), imazalil (449), imidacloprid (458), ipconazole (468), iprodione (470), isofenphos, lambda-cyhalothrin (198), mancozeb (496), maneb (497), metalaxyl (516), metalaxyl-M (517), metconazole (525), methiocarb (530), methyl-bromide (537), methyl-iodide (542), myclobutanil (564), nuarimol (587), omethoate (594), oxamyl (602), oxadixyl (601), oxine-copper (605), oxolinic acid (606), pencycuron (620), pefurazoate (618), phosmet (638), picoxystrobin (647), pirimicarb (651), prochloraz (659), procymidone (660), propamocarb (668), propiconazole (675), prothioconazole (685), pymetrozine (688), pyraclostrobin (690), pyrimethanil (705), pyroquilon (710), quintozene (716), silthiofam (729), spinosad (737), tebuconazole (761), tefluthrin (769), tetraconazole (778), thiabendazole (790), thiacloprid (791), thiamethoxam (792), thiodicarb (799), thiophanate-methyl (802), thiram (804), tolylfluanid (1,1-dichloro-N-[(dimethylamino)sulfonyl]-1-fluoro-N-(4-methylphenyl)methanesulfenamide), triadimenol (815), triazamate (818), triazophos (820), triazoxide (821), triticonazole (842), trifloxystrobin (832), 3-Iodo-N*2*-(2-methanesulfonyl-1,1-dimethyl-ethyl)-N*1*-[2-methyl-4-(1,2,2,2-tetrafluoro-1-trifluoromethyl-ethyl)-phenyl]-phthalamide (code NNI-0001), and a compound of 2-Pyridin-2-yl-2H-pyrazole-3-carboxylic acid (2-methylcarbamoyl-phenyl)-amide (code DKI-0001), such as 2-(3-Chloro-pyridin-2-yl)-5-trifluoromethyl-2H-pyrazole-3-carboxylic acid (4-chloro-2-isopropylcarbamoyl-6-methyl-phenyl)-amide, 2-(3-Chloro-pyridin-2-yl)-5-trifluoromethyl-2H-pyrazole-3-carboxylic acid (4-chloro-2-methyl-6-methylcarbamoyl-phenyl)-amide, 5-Bromo-2-(3-chloro-pyridin-2-yl)-2H-pyrazole-3-carboxylic acid (4-chloro-2-isopropylcarbamoyl-6-methyl-phenyl)-amide, 5-Bromo-2-(3-chloro-pyridin-2-yl)-2H-pyrazole-3-carboxylic acid (4-chloro-2-methyl-6- methylcarbamoyl-phenyl)-amide, and 3-Difluoromethyl-1-methyl-1Hpyrazole-4-carboxylic acid (2-bicyclopropyl-2-yl-phenyl)-amide.

The pesticide, such as nematicide, insecticide and fungicide, could be used in the present invention via the treatment (i) or the application (ii) as defined in the first aspect. Therefore, in an instance, a seed can be treated with abamectin and optionally one or more other pesticides, and then the chelating agent is applied to the locus of the abamectin treated seed before its planting, at its planting and/or during its growth. Further, the pesticides can also be applied to the locus of the plant ropagation material (including a pesticide treated plant propagation material) before it is planted, at its planting and/or during its growth.

The methods of applying the pesticide to the locus of the propagation material is via any suitable method, which ensures that the pesticide penetrates the soil, for example, nursery tray application, in furrow application, soil drenching, soil injection, drip irrigation, application through sprinklers or central pivot, incorporation into soil (broad cast or in band) are such methods.

In the event the components are applied individually, the time elapse between applications of the components to the locus of the plant should be such that on application of the second component the improved plant growth characteristics are demonstrated. The order of the application of the components is not critical, although preferred is the chelating agent followed by the pesticide (e.g. nematicide, macrocyclic lactone compound). The second component is applied within preferably 14, such as 10, for example, 5, more preferably 4, especially 3, advantageously 1, days of the first component.

The rate and frequency of use of the pesticide on the plant may vary within wide limits and depends on the specific pesticide, type of use, the nature of the soil, the method of application (pre- or post-emergence, etc.), the plant or pest to be controlled, the prevailing climatic conditions, and other factors governed by the method of application, the time of application and the target plant.

Typical application rate of abamectin to the locus of the crop plant is from 3 to 90 g per hectare (g/ha), especially from 6 to 60 g/ha, preferably from 9 to 40 g/ha, most preferably from 18 to 36 g/ha.

The pesticide may be applied once or several occasions in combination with the chelating agent (i.e. either simultaneously or in succession) during the growth of a plant depending on the plant and circumstances, for example, 1 to 6 or 1 to 4 occasions (for a tomato crop harvest, for example, the combination can be applied up to 4 times before harvest), and the amounts indicated above for abamectin application rates are for each application.

Typical application rates of a pesticide to a propagation material also vary depending on the specific use, specific seed and specific pesticide, and a skilled person can determine the appropriate rate depending on the specific circumstances so that the advantageous effects of the present invention are exhibited.

A description of the structure of the pesticides mentioned herein can be found in the e-Pesticide Manual, version 3.1, 13th Edition, Ed. CDC Tomlin, British Crop Protection Council, 2004-05.

The pesticide would protect the plant (including the plant propagation material) against known pests. It would control, i.e. to inhibit or destroy, pests occurring on plants, especially on useful plants (i.e., plants having a value, e.g., a monetary value to the grower, such as crops) and ornamentals in agriculture, in horticulture and in forestry, or on parts of such plants, such as the fruits, blossoms, leaves, stems, tubers or roots, while in some cases plant parts that grow later are still protected against those pests.

The combination of abamectin and a chelating agent has been found to be particularly effective in controlling nematodes, such as root-knot nematodes. An especially preferred combination is that comprising iron chelates of a EDDHA, and optionally other metals may also be present, such as sodium and potassium, as part of the chelating agent component. The action of the macrocyclic lactone compound together with a chelating agent goes far beyond their action individually, and the chelating agent is providing an enhancement of the activity of the pesticide. A synergistic effect exists whenever the action of, for example, the active ingredient combination of the compounds is greater than the sum of the actions of the active ingredients applied separately. This can be calculated, for example, by the Colby formula, as described in COLBY, S. R., "Calculating synergistic and antagonistic response of herbicide combinations", Weeds 15, pages 20-22, 1967.

In the treatment (i) or application (ii) as defined in the first aspect, the chelating agent is generally in the form of a formulation containing other customary formulation adjuvant because it allows, for example, less burdensome handleability and application A variety of formulation types exist: dry flowables (DF), liquid flowables (LF), true liquids (TL), emulsifiable concentrates (EC), suspension concentrates (SC), dusts (D), wettable powders (WP), suspoemulsions (SE), water-dispersible granules (WG) and others, such as encapsulations in polymeric substances. Some are registered for use only by commercial applicators using closed application systems, others are readily available for on-farm use as dusts, slurries, water-soluble bags, or liquid ready-to-apply formulations. Normally, however, commercial products are usually formulated as concentrates, where the end user will normally employ dilute formulations.

How the chelating agent is to be used will also determine the formulation type, for example, if the chelating agent is to be used as a seed treatment, then an aqueous composition is preferred.

The chelating agent and other agronomic chemicals (especially pesticides) can be part of a single composition and used simultaneously (i.e. they are mixed together—often referred to as "a pre-mix"), or can be separate products and used separately (e.g. sequentially). In the event they are separate products, they can be mixed together shortly before treatment (i) or application (ii) by the user.

It is often more practical, where possible, for commercially available fomulations of the chelating agent and agronomic chemicals to be brought together in the desired mixing ratio in a container (often referred to as a "tank mixture") in water shortly before application.

The present invention, therefore, also relates to an agrochemical composition (e.g. "tank mixture" and "pre-mix") for applying to the locus of a crop plant or treatment of plant propagation material comprising (A) a chelating agent and (B) one or more pesticides (such as an insecticide, nematicide, acaricide), with the proviso that the composition consisting of, as active ingredients, abamectin and N-phosphonomethyl valine is excluded.

In an embodiment, the chelating agent and one or more agronomic chemicals (especially pesticides, such as nematicides (e.g. abamectin)) are used in single composition that has been specifically formulated, the composition may be in the form one of the formulation types mentioned above, the type of formulation being chosen in accordance with the intended objectives and the prevailing circumstances; the chelating agent and agronomic chemical are used together with at least one of the adjuvants customary in formulation technology, such as extenders, e.g., solvents or solid carriers, or surface-active compounds (surfactants).

Suitable formulation adjuvants are, for example, solid carriers, solvents, stabilisers, slow-release adjuvants, dyes and optionally surface-active substances (surfactants). Suitable carriers and adjuvants in this case include all substances customarily used in crop projection products, especially in products for controlling snails and slugs. Suitable adjuvants, such as solvents, solid carriers, surface-active compounds, non-ionic surfactants, cationic surfactants, anionic surfactants and further adjuvants in the compositions used in accordance with the invention are, for example, the same as those described in EP-A-736252; are fully incorporated by reference herein for their disclosure relating to useful formulation adjuvants.

The compositions as a rule comprise 0.1 to 99%, in particular 0.1 to 95% of the combination and 1 to 99.9%, in particular 5 to 99.9%, of at least one solid or liquid auxiliary, it being possible as a rule for 0 to 25%, in particular 0.1 to 20%, of the composition to be surfactants (% is in each case percent by weight). While concentrated compositions are more preferred as commercial goods, the end user as a rule uses dilute compositions that comprise considerably lower concentrations of the combination. Preferred compositions are composed, in particular, as follows (%=percent by weight):

Emulsifiable Concentrates:

| combination: | 1 to 90%, preferably 5 to 20% |
|---|---|
| surfactant: | 1 to 30%, preferably 10 to 20% |
| solvent: | balance |

Dusts:

| combination: | 0.1 to 10%, preferably 0.1 to 1% |
|---|---|
| solid carrier: | 99.9 to 90%, preferably 99.9 to 99% |

Suspension Concentrates:

| combination: | 5 to 60%, preferably 10 to 40% |
|---|---|
| surfactant: | 1 to 40%, preferably 2 to 30% |
| water: | balance |

Wettable Powders:

| combination: | 0.5 to 90%, preferably 1 to 80% |
|---|---|
| surfactant: | 0.5 to 20%, preferably 1 to 15% |
| solid carrier: | balance |

Granules:

| combination: | 0.5 to 60%, preferably 3 to 40% |
|---|---|
| solid carrier: | 99.5 to 70%, preferably 97 to 85% |

Examples of specific formulation examples for use in crop protection are given below (%=percent by weight):

EXAMPLE F1

Emulsifiable Concentrates

|  | a) | b) | c) |
|---|---|---|---|
| combination | 25% | 40% | 40% |
| Calcium dodecylbenzenesulphonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| N-methyl pyrrolidone | 25% | 35% | 40% |
| Xylene mixture | 40% | 5% | 10% |

Mixing of finely ground macrocyclic lactone compound, chelating agent and additives gives an emulsion concentrate, which by dilution with water, affords emulsions of the desired concentration.

EXAMPLE F2

Solutions

|  | a) | b) | c) |
|---|---|---|---|
| combination | 40% | 10% | 5% |
| Ethylene glycol monomethyl ether | 10% | 20% | — |
| Polyethylene glycol (MW 400) | 15% | 70% | — |
| N-methylpyrrolid-2-one | 35% | — | — |
| Epoxidized coconut oil | — | — | 1% |
| Aliphatic hydrocarbon (boiling range: 160-190°) | — | — | 94% |

Mixing of finely ground macrocyclic lactone compound, chelating agent and additives gives a solution suitable for use in the form of microdrops.

EXAMPLE F3

Granules

|  | a) | b) | c) | d) |
|---|---|---|---|---|
| combination | 5% | 10% | 8% | 21% |
| Kaolin | 94% | — | 79% | 54% |
| Finely divided silicic acid | 1% | — | 13% | 7% |
| Attapulgite | — | 90% | — | 18% |

The macrocyclic lactone compound and chelating agent are dissolved in dichloromethane, the solution is sprayed onto the mixture of carriers and the solvent is evaporated under reduced pressure.

EXAMPLE F4

Wettable Powder

|  | a) | b) | c) |
|---|---|---|---|
| combination | 25% | 50% | 75% |
| Sodium lignosulphonate | 5% | 5% | — |
| Sodium lauryl sulphate | 3% | — | 5% |
| Sodium diisobutylnaphthalene sulphonate | — | 6% | 10% |
| Octylphenol polyethylene glycol ether (7-8 mol of EO) | — | 2% | — |
| Finely divided silicic acid | 5% | 10% | 10% |
| Kaolin | 62% | 27% | — |

Macrocyclic lactone compound, chelating agent and additives are mixed and the mixture is ground in a suitable mill. This gives wettable powders which can be diluted with water to give suspensions of the desired concentration.

EXAMPLE F5

Extruder Granules

| | |
|---|---|
| combination | 60% |
| Sodium lignosulphonate | 10% |
| Carboxymethylcellulose | 1% |
| Kaolin | 29% |

Macrocyclic lactone compound, chelating agent and additives are mixed, the mixture is ground, moistened with water, extruded and granulated, and the granules are dried in a stream of air.

EXAMPLE F6

Coated Granules

| | |
|---|---|
| combination | 3% |
| Polyethylene glycol (MW 200) | 3% |
| Kaolin | 94% |

In a mixer, the finely ground macrocyclic lactone compound and chelating agent are applied uniformly to the kaolin which has been moistened with polyethylene glycol. This gives dust-free coated granules.

EXAMPLE F7

Suspension Concentrate

| | |
|---|---|
| combination | 40% |
| Ethylene glycol | 10% |
| Nonylphenol polyethylene glycol ether (15 mol of EO) | 6% |
| Sodium lignosulphonate | 10% |
| Carboxymethylcellulose | 1% |
| Aqueous formaldehyde solution (37%) | 0.2% |
| Aqueous silicone oil emulsion (75%) | 0.8% |
| Water | 32% |

Mixing of finely ground macrocyclic lactone compound, chelating agent and additives gives a suspension concentrate which, by dilution with water, affords suspensions of the desired concentration.

The composition may also comprise further solid or liquid adjuvants, such as stabilisers, e.g., vegetable oils or epoxidised vegetable oils (e.g., epoxidised coconut oil, rapeseed oil or soybean oil), antifoams, e.g., silicone oil, preservatives, viscosity regulators, binders and/or tackifiers as well as fertilisers or other active ingredients for obtaining special effects, e.g., acaricides, bactericides, fungicides, nematicides, molluscicides or selective herbicides.

The following Examples are given by way of illustration and not by way of limitation of the invention.

BIOLOGICAL EXAMPLES

%=Percent by Weight Unless Otherwise Indicated

Experiment 1:

Tomato plants are transplanted into a field infested with nematodes (*Pratylenchus* spp.) and treated with the treatments indicated in Table I below 1, 14, 27 and 40 days after transplantation. The products are applied by drenching 100 ml spray solution per plant. Plot size is 24 m$^2$ with 4 replicates. At harvest (up to 19 weeks later), all tomatoes are collected and weighted. The check is an untreated control.

TABLE I

| Treatments | % damage of roots | Total average weight of tomatoes per treatment in kg | % yield increase over check |
|---|---|---|---|
| Check | 40.8 | 701 | — |
| EDTA 500 g ai/ha | 25.8 | 784 | 12 |
| EDTA 1000 g ai/ha | 22.5 | 817 | 17 |

Experiment 2:

Tomato plants are transplanted into a field infested with nematodes (*Pratylenchus* spp.) and treated with the treatments indicated in Table II below 1, 14, 27 and 40 days after transplantation. The products are applied by drenching 100 ml spray solution per plant. Plot size is 24 m$^2$ with 4 replicates. At harvest (up to 19 weeks later), all tomatoes are collected and weighted. The check is an untreated control.

TABLE II

| Treatments | % damage of roots | Total average weight of tomatoes per plant in gr | % yield increase over check |
|---|---|---|---|
| Check | 30.8 | 3143 | — |
| EDDHA 500 g ai/ha | 18.5 | 3500 | 11 |
| EDDHA 1000 g ai/ha | 13.8 | 3695 | 18 |

Experiment 3:

Tomato plants are transplanted into a field infested with nematodes (*Meloidogyne* spp.) and treated with the treatments indicated in Table III below 1, 18, 32 and 46 days after transplantation. The products are applied by drenching 100 ml spray solution per plant. Plot size is 36.7 m$^2$ with 4 replicates. At harvest (up to 19 weeks later), all tomatoes are collected and weighted. The check is an untreated control.

TABLE III

| Treatments | % root galling | Total average weight of tomatoes per 100 plant in kgr | % yield increase over check |
|---|---|---|---|
| Check | 83.9 | 226 | — |
| EDDHA 500 g ai/ha | 35 | 255 | 13 |
| EDDHA 1000 g ai/ha | 26.1 | 265 | 17 |

Experiment 4:

Tomato plants are transplanted into a field infested with nematodes (*Meloidogyne* spp.) and treated with the treatments indicated in Table IV below 1, 18, 32 and 46 days after transplantation. The products are applied by drenching 100 ml spray solution per plant. Plot size is 42.7 m$^2$ with 4 replicates. At harvest (up to 19 weeks later), all tomatoes are collected and weighted. The check is an untreated control.

TABLE IV

| Treatments | % average root galling | Total average weight of tomatoes per 100 plants in kg | % yield increase over check |
|---|---|---|---|
| Check | 79.8 | 328 | — |
| EDTA 500 g ai/ha | 34.4 | 349 | 6 |
| EDTA 1000 g ai/ha | 23.7 | 360 | 10 |

Experiment 5:

110 grams of dry sandy soil is put into plastic cups. The soil is treated by adding 25 ml of water containing given concentrations (in ppm) of chemicals to the soil. The soil and water is carefully mixed and thereafter 1 ml of water containing 12,000 eggs of *Meloidogyne* is added. After 15 days of incubation, the samples are analyzed for live 2nd stage nematodes by sieving the sand and rinsing with tap water. The amount of rinseate is adjusted to 20 ml. From the 20 ml, 3 samples of 1 ml are taken and nematodes counted, using a counting chamber.

| Treatments | Concentration of applied solution in ppm | Number of live 2nd stage nematodes | % reduction of live stages | Expected according to Colby formula |
|---|---|---|---|---|
| Check | | 1651 | | |
| Vertimec | 3 | 1080 | 34.6 | |
| Sequestrene | 3 | 1648 | 0.2 | |
| EDDHA | 3 | 1649 | 0.1 | |
| EDTA | 3 | 1650 | 0.1 | |
| Vertimec + Sequestrene | 3 + 3 | 690 | 58.2 | 34.7 |
| Vertimec + EDDHA | 3 + 3 | 735 | 55.5 | 34.7 |
| Vertimec + EDTA | 3 + 3 | 745 | 54.9 | 34.6 |

Experiment 6:

50 grams of dry clay soil is put into plastic cups. The soil is treated by adding 50 ml of water containing given concentrations (in ppm) of chemicals to the soil. The soil and water is carefully mixed, and thereafter 1 ml of water containing 10,000 eggs of *Meloidogyne* is added. After 15 days of incubation, the samples are analyzed for live 2nd stage nematodes by sieving the clay, and rinsing with tap water. The amount of rinseate is adjusted to 20 ml. From the 20 ml, 3 samples of 1 ml are taken and nematodes counted, using a counting chamber.

| Treatments | Concentration of applied solution in ppm | Number of live 2nd stage nematodes | % reduction of live stages | Expected according to Colby formula |
|---|---|---|---|---|
| Check | | 1201 | | |
| Vertimec | 3 | 593 | 50.6 | |
| Sequestrene | 3 | 1167 | 2.8 | |
| EDDHA | 3 | 1197 | 0.3 | |
| EDTA | 3 | 1200 | 0.1 | |
| Vertimec + Sequestrene | 3 + 3 | 270 | 77.5 | 52.0 |
| Vertimec + EDDHA | 3 + 3 | 274 | 77.2 | 50.8 |
| Vertimec + EDTA | 3 + 3 | 273 | 77.3 | 50.7 |

The invention claimed is:

1. A method of reducing damage to plant propagation material and plant organs which grow at a later time by a representative of the class Nematoda, which method comprises (i) sowing or planting plant propagation material treated with effective amounts of (A) a chelating agent and (B) abamectin before the material is sown or planted, or (ii) applying effective amounts of (A) a chelating agent and (B) abamectin to the locus of the material or the treated material defined in (i) before its planting, and/or at its planting and/or during its growth; and reducing damage to the treated plant propagation material and plant organs which grow at a later time, wherein the chelating agent is an amino polycarboxylic acid and provided, when the chelating agent is metallated, the metal is Fe.

2. The method according to claim 1 wherein the plant propagation material is selected from the crops vegetables, citrus, soybeans, cotton, corn, potato, sugar beets, sugar cane, or cereals.

3. The method according to claim 1 wherein the plant propagation material is a seed.

4. The method according to claim 1 wherein the metallated chelating agent is an iron chelate.

5. The method according to claim 1 wherein the chelating agent is selected from N,N'-ethylene-bis(hydroxyphenyl)glycine (EDDHA), ethylenediaminebis(2-hydroxy-methylphenylacetic acid) (EDDHMA), N,N'-ethylenebis(2-hydroxy-5-sulfophenyl)glycine (EDDHSA), ethylenediaminetetraacetic acid (EDTA), N-(2-hydroxyethyl)-ethylenediaminetetraacetic acid (HEDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), glycoletherdiaminetetracetic acid (GEDTA) and ethylenediaminedisuccinic acid (EDDS), and salts thereof.

6. A method of improving the control of soil-inhabiting pests towards a plant by a pesticide, which comprises (i) sowing or planting plant propagation material treated with effective amounts of (A) a chelating agent and (B) a pesticide comprising abamectin, before the material is sown or planted, or (ii) applying effective amounts of (A) a chelating agent and (B) a pesticide comprising abamectin, to the locus of the material or the treated material defined in (i) before its planting, and/or at its planting and/or during its growth; and reducing damage to the treated plant propagation material and plant organs which grow at a later time, wherein the chelating agent is an amino polycarboxylic acid and provided, when the chelating agent is metallated, the metal is Fe.

* * * * *